(12) United States Patent
Berg et al.

(10) Patent No.: US 6,291,458 B1
(45) Date of Patent: Sep. 18, 2001

(54) MORPHOLINOBENZAMIDE SALTS

(75) Inventors: Stefan Berg, Ekerö (SE); Daniel Sohn, Northborough, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/621,387

(22) Filed: Jul. 21, 2000

Related U.S. Application Data

(62) Continuation of application No. PCT/SE00/00079, filed on Jan. 14, 2000, which is a continuation-in-part of application No. 09/171,577, filed as application No. PCT/SE98/01390 on Jul. 15, 1998.

(30) Foreign Application Priority Data

Jul. 2, 1997 (SE) .................................................... 9702799
Jan. 22, 1999 (SE) .................................................... 9900190

(51) Int. Cl.[7] ...................... A61K 31/5377; A61P 25/22; C07D 413/14
(52) U.S. Cl. ....................................... 514/235.8; 544/121
(58) Field of Search ........................... 544/121; 514/235.8

(56) References Cited

U.S. PATENT DOCUMENTS

| | | |
|---|---|---|
| 5,196,454 | 3/1993 | Crauert et al. . |
| 6,124,283 * | 9/2000 | Berg et al. ........................ 514/227.8 |

FOREIGN PATENT DOCUMENTS

| | | |
|---|---|---|
| 402923 | 12/1990 | (EP) . |
| 533266 | 3/1993 | (EP) . |
| 533267 | 3/1993 | (EP) . |
| 533268 | 3/1993 | (EP) . |
| 2273930 | 7/1994 | (GB) . |
| 9413659 | 6/1994 | (WO) . |
| 9421619 | 9/1994 | (WO) . |
| 9511243 | 4/1995 | (WO) . |
| 9734883 | 9/1997 | (WO) . |

* cited by examiner

*Primary Examiner*—Robert W. Ramsuer
(74) *Attorney, Agent, or Firm*—White & Case LLP

(57) ABSTRACT

The present invention relates to pharmaceutically acceptable salts of the compound of formula I or solvates of said salt in which the compound of formula I is as the (R)-enantiomer, the (S)-enantiomer or the racemate,

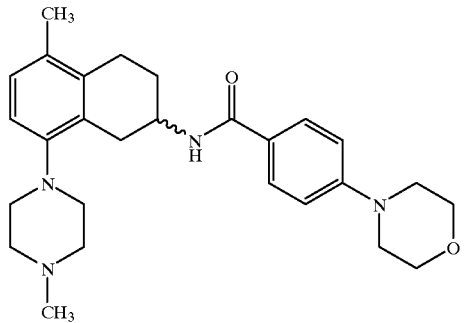

(I)

a process for their preparation, pharmaceutical formulations containing said therapeutically active compounds and to the use of said active compounds in therapy.

20 Claims, No Drawings

MORPHOLINOBENZAMIDE SALTS

CROSS-REFERENCE TO RELATED APPLICATIONS

This application is a continuation of International PCT Application No. PCT/SE00/00079 filed on Jan. 14, 2000, and which is a continuation-in-part of U.S. application Ser. No. 09/171,577 filed on Oct. 21, 1998 (pending), which is a 371 of PCT/SE98/01390 filed on Jul. 15, 1998.

FIELD OF THE INVENTION

The present invention relates to new pharmaceutically acceptable salts of N-[5-methyl-8-(4-methylpiperazin-1-yl)-1,2,3,4-tetrahydro-2-naphthyl]-4-morpholinobenzamide as the (R)-enantiomer, the (S)-enantiomer or the racemate or as solvates of said salts, a process for their preparation, pharmaceutical formulations containing said salts or solvates and to the use of said active salts or solvates in therapy.

An object of the invention is to provide compounds for therapeutic use, especially compounds having a selective effect at a subgroup of 5-hydroxytryptamine receptors, designated the $h5-HT_{1B}$-receptor (previously called the $5-HT_{1D\beta}$-receptor) in mammals including man, which compounds are easily formulated into pharmaceutical formulations.

It is also an object of the invention to provide compounds with a therapeutic effect after oral administration.

PRIOR ART

Different classes of piperazinyl substituted benzanilide derivatives as $5-HT_{1D}$ antagonists are disclosed in inter alia EP 533266, EP 533267, EP 533268, GB 2273930 and WO 95/11243.

WO 94/13659 discloses an extremely broad class of fused benzo compounds having a para substituted piperidyl or piperazinyl radical in the aromatic ring, said class or compounds is stated to bind to the $5-HT_{1A}$ receptor.

WO 94/21619 discloses a fully aromatic naphthalene ring system which may be substituted with a piperidyl or piperazinyl group, said compounds are also stated to be potent serotonin ($5HT_1$) agonists and antagonists.

EP 402923 discloses 2-aminoalkyl or alkylenaromatic substituted 1,2,3,4-tetrahydronaphthalene derivatives having a further nitrogen substitution in the 5 position in the tetraline ring, said compounds act as dopamine agonists.

BACKGROUND OF THE INVENTION

Various central nervous system disorders such as depression, anxiety, etc. appear to involve the disturbance of the neurotransmitters noradrenaline (NA) and/or 5-hydroxytryptamine(5-HT), the latter also known as serotonin. The drugs most frequently used in the treatment of depression are believed to act by improving the neurotransmission of either or both of these physiological agonists. It appears that the enhancement of 5-HT neurotransmission primarily affects the depressed mood and anxiety, whereas the enhancement of noradrenaline neurotransmission affects the retardation symptoms occurring in depressed patients.

Serotonin, or 5-HT, activity is thought to be involved in many different types of psychiatric disorders. For instance it is thought that an increase in 5-HT activity is associated with anxiety, while a decrease in 5-HT release has been associated with depression. Serotonin has in addition been implicated in such diverse conditions as eating disorders, gastrointestinal disorders, cardiovascular regulation and sexual behavior.

The compound of formula I below in base form has an extremely low solubility in water and a slow release rate which rate is pH dependent, i.e. the rate is different in the stomach and the intestines. From a pharmaceutical formulation point of view it is very difficult to dissolve the base rapidly enough and maintain the same dissolved in the gastric juice until a sufficient amount of substance has been absorbed.

The 5-HT Receptors

The various effects of 5-HT may be related to the fact that serotoninergic neurons stimulate the secretion of several hormones, e.g. cortisol, prolactin, B-endorphin, vasopressin and others. The secretion of each of these other hormones appears to be regulated on a specific basis by several different 5-HT (serotonin) receptor subtypes. With the aid of molecular biology techniques, to date these receptors have been classified as $5-HT_1$, $5-HT_2$, $5-HT_3$, $5-HT_4$, $5-HT_5$, $5-HT_6$ and $5-HT_7$ with the $5-HT_1$ receptor further divided into the $5-HT_{1A}$, $5-HT_{1B}$, $5-HT_{1D}$, $5-HT_{1E}$ and $5-HT_{1F}$ subtypes. Each receptor subtype is involved in a different serotonin function and has different properties.

Regulation of the 5-HT transmission

The release of 5-HT at the nerve terminals is feedback-regulated by two different subtypes of 5-HT receptors. Inhibitory $5-HT_{1A}$ autoreceptors are located on the cell bodies in the raphe nuclei which upon stimulation by 5-HT decrease the impulse propagation in the 5-HT neurons and thereby reducing the 5-HT release at the nerve terminals. Another subtype of inhibitory 5-HT receptors is located on the 5-HT nerve terminals, the $h5-HT_{1B}$ receptors (in rodents the $r5-HT_{1B}$ receptors) which regulate the synaptic concentration of 5-HT by controlling the amount of 5-HT that is released. An antagonist of these terminal autoreceptors thus increases the amount of 5-HT released by nerve impulses as has been shown in both in vitro and in vivo experiments.

The use of an antagonist of the terminal $h5-HT_{1B}$ autoreceptor will accordingly increase the synaptic 5-HT concentration and enhance the transmission in the 5-HT system. It would thus produce an antidepressant effect making it useful as a medication for depression.

Other localizations of $h5-HT_{1B}$ receptor subtype also exist. A large part of these postsynaptic receptors appear to be located on nerve terminals of other neuronal systems (so called heteroreceptors). Since the $h5-HT_{1B}$ receptor mediates inhibitory responses an antagonist of this receptor subtype might also increase the release of other neurotransmitters than 5-HT.

Compounds having $h5-HT_{1B}$ activity may according to well known and recognised pharmacological tests be divided into full agonists, partial agonists and antagonists.

DISCLOSURE OF THE INVENTION

The object of the present invention is to provide compounds having a selective effect at the $h5-HT_{1B}$ receptor, preferably antagonistic properties, as well as having a good bioavailability and which may easily be formulated into pharmaceutical formulations. The compounds according to the invention have surprisingly solved the above problem since they are dissolved rapidly enough and are maintained dissolved in the gastric juice until a sufficient amount of substance has been absorbed Accordingly, the present invention provides pharmaceutically acceptable salts of the compound of formula I or solvates of said salt in which the compound of formula I is as the (R)-enantiomer, the (S)-enantiomer or the racemate,

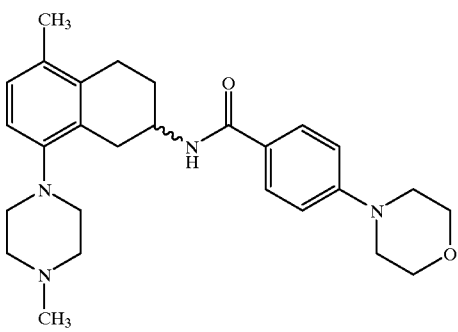

(I)

with the proviso that (R)-N-[5-methyl-8-(4-methylpiperazin-1-yl)-1,2,3,4-tetrahydro-2-naphthyl]-4-morpholinobenzamide hydrogen (2S,3S)-tartrate, (R)-N-[5-methyl-8-(4-methylpiperazin-1-yl)-1,2,3,4-tetrahydro-2-naphthyl]-4-morpholinobenzamide hydrogen (2R,3R)-tartrate, (R)-N-[5-methyl-8-(4-methylpiperazin-1-yl)-1,2,3,4-tetrahydro-2-naphthyl]-4-morpholinobenzamide benzenesulfonate, (R)-N-[5-methyl-8-(4-methylpiperazin-1-yl)-1,2,3,4-tetrahydro-2-naphthyl]-4-morpholinobenzarnide hydrogen 1,2-ethanedisulfonate, (R)-N-[5-methyl-8-(4-methylpiperazin-1-yl)-1,2,3,4-tetrahydro-2-naphthyl]-4-morpholinobenzamide hydrogen maleate, (R)-N-[5-methyl-8-(4-methylpiperazin-1-yl)-1,2,3,4-tetrahydro-2-naphthyl]-4-morpholinobenzarnide hydrogen sulfate, (R)-N-[5-methyl-8-(4-methylpiperazin-1-yl)-1,2,3,4-tetrahydro-2-naphthyl]-4-morpholinobenzamide D-gluconate, (R)-N-[5-methyl-8-(4-methylpiperazin-1-yl)-1,2,3,4-tetrahydro-2-naphthyl]-4-morpholinobenzamide hydrogen succinate, (R)-N-[5-methyl-8-(4-methylpiperazin-1-yl)-1,2,3,4-tetrahydro-2-naphthyl]-4-morpholinobenzamide methanesulfonate, (R)-N-[5-methyl-8-(4-methylpiperazin-1-yl)-1,2,3,4-tetrahydro-2-naphthyl]-4-morpholinobenzamide hydrogen (S)-maleate, (R)-N-[5-methyl-8-(4-methylpiperazin-1-yl)-1,2,3,4-tetrahydro-2-naphthyl]-4-morpholinobenzamide dihydrogen citrate and (R)-N-[5-methyl-8-(4-methylpiperazin-1-yl)-1,2,3,4-tetrahydro-2-naphthyl]-4-morpholinobenzamide hydrochloride are excluded, which salts possess a high selective effect at the h5-HT$_{1B}$ receptor, are easily formulated into pharmaceutical formulations and also show sufficient bioavailability after oral administration.

The preferred enantiomers are the (R)-enantiomers.

Preferred compounds are (R)-N-[5-methyl-8-(4-methylpiperazin-1-yl)-1,2,3,4-tetrahydro-2-naphthyl]-4-morpholinobenzamide L-lactate, (R)-N-[5-methyl-8-(4-methylpiperazin-1-yl)-1,2,3,4-tetrahydro-2-naphthyl]-4-morpholinobenzamide dihydrobromide, (R)-N-[5-methyl-8-(4-methylpiperazin-1-yl)-1,2,3,4-tetrahydro-2-naphthyl]-4-morpholinobenzamide monohydrobromide and (R)-N-[5-methyl-8-(4-methylpiperazin-1-yl)-1,2,3,4-tetrahydro-2-naphthyl]-4-morpholinobenzamide dihydrochloride.

Both organic and inorganic acids can be employed to form non-toxic pharmaceutically acceptable acid addition salts according to the invention. Illustrative acids are sulfuric, nitric, phosphoric, oxalic, hydrochloric, forrnic, hydrobromic, citric, acetic, lactic, tartaric, dibenzoyltartaric, diacetyltartaric, palmoic, ethanedisulfonic, sulfamic, succinic, propionic, glycolic, malic, gluconic, pyruvic, phenylacetic, 4-aminobenzoic, anthranilic, salicylic, 4-aminosalicylic, 4-hydroxybenzoic, 3,4-dihydroxybenzoic, 3,5-dihydroxybenzoic, 3-hydroxy-2-naphthoic, nicotinic, methanesulfonic, ethanesulfonic, hydroxyethanesulfonic, benzenesulfonic, p-toluenesulfonic, sulfanilic, naphthalenesulfonic, ascorbic, cyclohexylsulfamic, fumaric, maleic and benzoic acids. The compound of formula I can form hemi- mono-, sesqui-, di- or trisalts or any other salt combination therein between of the above acids, if applicable. These salts are readily prepared by methods known in the art.

The preferred solvates of this invention are the hydrates. Other solvates may be formed from solvents such as ethyl acetate, ethanol or acetone. The solvates of the salts are readily prepared by methods known in the art.

Pharmaceutical Formulations

In a second aspect the present invention provides easily formulated pharmaceutical formulations comprising as active ingredient a therapeutically effective amount of a pharmaceutically acceptable salt of the compound of formula I or a solvate of said salt as an enantiomer or a racemate, or a combination of such salts and/or solvates, optionally in association with diluents, excipients or inert carriers.

According to the present invention the compound of the invention will normally be administered orally, rectally or by injection, in the form of pharmaceutical formulations comprising the active ingredient either as a pharmaceutically acceptable non-toxic acid addition salt, e.g. hydrochlorides, hydrobromides, lactates, acetates, phosphates, sulfates, sulfamates, citrates, tartrates, oxalates and the like or as a solvate of such salt in a pharmaceutically acceptable dosage form. The dosage form may be a solid, semisolid or liquid preparation. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical formulations containing the compound of the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the person skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or polyethylene glycol. Hard gelatine capsules may contain granules of the active substance using either the above mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.1% to about 20% by weight of the active substance herein described, the balance being sugar and mixture of ethanol, water, glycerol and propylene glycol. Optionally such liquid preparations may contain colouring agents, flavouring agents, saccharin and carboxymethylcellulose as a thickening agent or other excipients known to the person skilled in the art.

Solutions for parenteral applications by injection can be prepared in an aqueous solution of a water-soluble pharmaceutically acceptable salt of the active substance, preferably in a concentration of from about 0.1% to about 10% by weight. These solutions may also contain stabilizing agents and/or buffering agents and may conveniently be provided in various dosage unit ampoules.

Suitable daily doses of the compound of the invention in therapeutical treatment of humans are about 0.01–100 mg/kg bodyweight at peroral administration and 0.001–100 mg/kg bodyweight at parenteral administration.

The compound of the invention may be used in a combination with a 5-HT reuptake inhibitor, such as fluoxetine, paroxetine, citalopram, clomipramine, sertraline, alaproclate or fluvoxamin, preferably paroxetine or citalopram. Another possible combination is to use the compound of the invention together with a monoamine oxidase inhibitor, such as moclobemide, tranylcypramine, brofaromide or phenelzine, preferably moclobemide or phenelzine. Still another possible combination is the compound of the invention together with a 5-HT$_{1A}$ antagonist, such as one of the compounds disclosed in WO 96/33710, preferably (R)-5-carbamoyl-3-(N,N-dicyclobutylamino)-8-fluoro-3,4-dihydro-2H-1-benzopyran.

Medical and Pharmaceutical Use

In a further aspect the present invention provides the use of the compounds of the invention in therapy as a h5-HT$_{1B}$ antagonists, partial agonists or full agonists, preferably as antagonists and the use in the treatment of 5-hydroxytryptamine mediated disorders. Examples of such disorders are disorders in the CNS such as mood disorders (depression, major depressive disorder, major depressive episodes, dysthymia, seasonal affective disorder, depressive phases of bipolar disorder), anxiety disorders (obsessive compulsive disorder, panic disorder with/without agoraphobia, social phobia, specific phobia, generalized anxiety disorder, posttraumatic stress disorder), personality disorders (disorders of impulse control, trichotellomania), obesity, anorexia, bulimia, premenstrual syndrome, sexual disturbances, alcoholism, tobacco abuse, autism, attention deficit, hyperactivity disorder, migraine, memory disorders (age associated memory impairment, presenile and senile dementia), pathological aggression, schizophrenia, endocrine disorders (e g hyperprolactinaemia), stroke, dyskinesia, Parkinson's disease, thermoregulation, pain, and hypertension. Other examples of hydroxytryptamine mediated disorders are urinary incontinence, vasospasm and growth control of tumors (e g lung carcinoma).

Methods of Preparation

The present invention also relates to processes for preparing compounds of the nvention.

Methods of Preparation of Intermediates (i) Benzylation of the compound of formula II, either as a racemate or as an enantiomer,

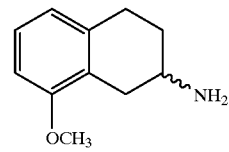

(II)

to obtain a compound of formula III may be carried out by reaction with a suitable benzylation agent e.g. a benzyl halide such as benzyl bromide or benzyl chloride or an activated alcohol e.g. benzylesylate or benzyl tosylate. The reaction may be carried out using a salt or the base of compound II in a suitable solvent e.g. N,N-dimethylformamide, acetone or acetonitrile with a suitable base e.g. NaOH, NaHCO$_3$, K$_2$CO$_3$ or a trialkylamine such as triethylamine at a temperature within the range of +20° C. to +150 ° C. The presence of a suitable catalyst e.g. potassium iodide or sodium iodide, may increase the speed of the reaction.

(ii) Demethylation of the compound of formula III

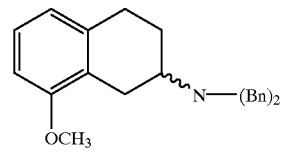

(III)

to obtain a compound of formula IV may be carried out by treating the compound with an acidic reagent such as aqueous HBr, HI, HBr/CH$_3$COOH, BBr$_3$, AlCl$_3$, pyridine-HCl or with a basic nucleophilic reagent such as CH$_3$C$_6$H$_4$S$^-$ or C$_2$H$_5$S$^-$ in a suitable solvent. Suitable solvents may be methylene chloride or chloroform and the reaction may occur between −78° C. and +60° C.

(iii) Conversion of the compound of formula IV to a compound of formula V

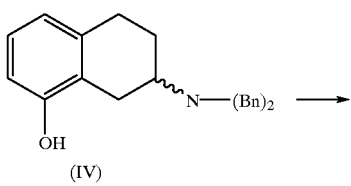

(IV)

-continued

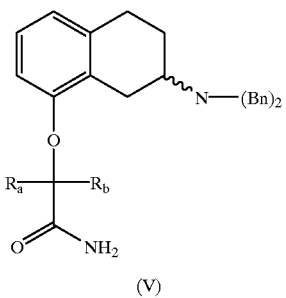

(V)

may be carried out by the reaction with a compound of formula VI

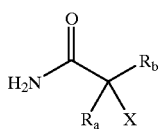

(VI)

where X stands for a leaving group, e.g. a halogen such as chlorine, bromine or iodine or an alkane- or arenesulfonyloxy group such as a p-toluenesulfonyloxy group and $R_a$ and $R_b$ are hydrogen or a lower alkyl group e.g. methyl. The process may be carried out with a salt of the compound of formula IV obtained by reaction with a base such as $K_2CO_3$, $Na_2CO_3$, KOH, NaOH, BuLi or NaH. The reaction may be conducted in a suitable solvent e.g. an aprotic solvent such as dioxane, N,N-dimethylformamide, tetrahydrofuran, toluene, benzene or petroleum ether and the reaction may occur between +20° C. and +150° C.

(iv) Rearrangement of a compound of formula V to a compound of formula VII

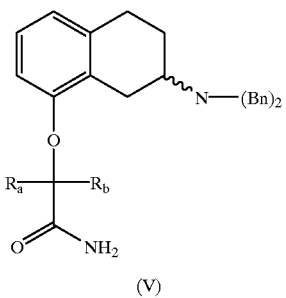

(V)

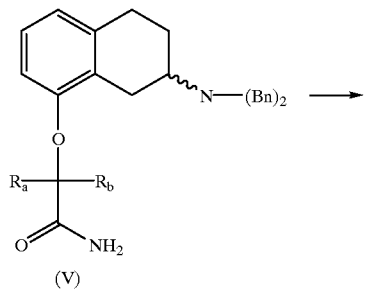

(VII)

may be carried out in a suitable solvent e.g. an aprotic solvent such as NN dimethylformamide, dioxane, 1,1,3,3-tetramethylurea, tetrahydrofuran or hexamethylphosphoric triamide with a suitable base e.g. $K_2CO_3$, KOH, potassium tert-butoxide or NaH at a temperature within the range of +20° C. to +150° C. The presence of a cosolvent such as 1,3-dimethyl-3,4,5,6-tetrahydro-2(1H)-pyrimidone or hexamethylphosphoric triamide in appropriate concentration in the solvent may increase the speed of the reaction.

(v) Hydrolysis of a compound of formula VII to a compound VIII may be carried out under acidic conditions using acids such as $H_2SO_4$, HCl or HBr in a suitable solvent e.g. $H_2O$, ethanol, methanol or mixtures thereof and the reaction may occur between +20° C. and +100° C. or under basic conditions using bases such as NaOH or KOH in a suitable solvent e.g. $H_2O$, ethanol, methanol or mixtures thereof and the reaction may occur between +20° C. and +100° C.

(vi) Conversion of compound of formula VIII to a compound of formula IX

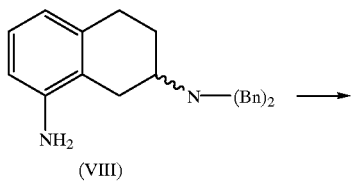

(VIII)

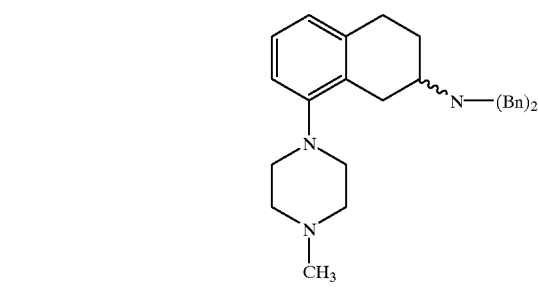

(IX)

may be carried out by reaction with a compound of formula X.

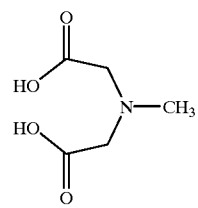

(X)

The process may be carried out in a suitable solvent e.g. an aprotic/anhydrous solvent such as tetrahydrofuran or N,N-dimethylformamide in the presence of a coupling reagent such as N,N'-carbonyldiimidazole and the reaction may occur between +20° C. and +130° C. The reaction is followed by the reduction of the imide with a suitable reducing agent e.g. LiAlH$_4$ in a suitable solvent e.g. diethyl ether or tetrahydrofuran at a temperature between +20° C. and reflux.

(vii) Halogenation of the compound of formula IX

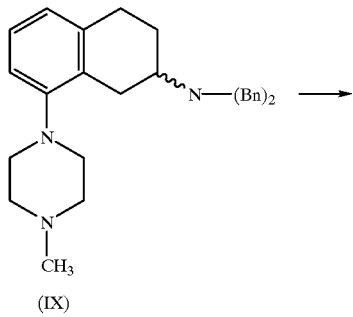
(IX)

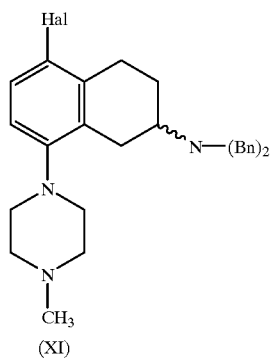
(XI)

to obtain a compound of formula XI may be performed by aromatic electrophilic substitution using a suitable halogenation agent such as Br$_2$, Cl$_2$, I$_2$, ICl, or SO$_2$Cl$_2$. The reaction may be carried out using the salt or the base of the compound IX in an appropriate solvent e.g. acetic acid, HCl/ethanol or water with or without a suitable base e.g. alkali metal acetate such as sodium acetate and at a reaction temperature between –20° C. and room temperature.

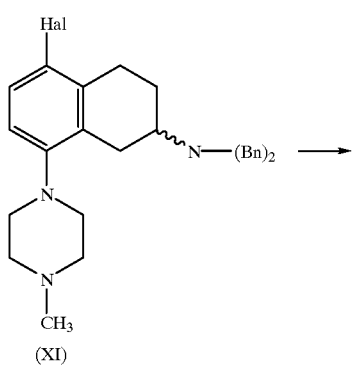
(XI)

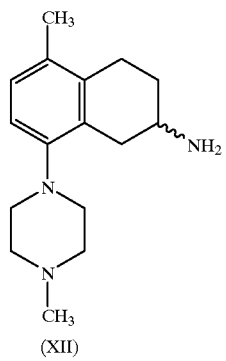
(XII)

(viii) Conversion of the compound of formula XI to a compound of formula XII may be carried out by a metal-halogen exchange, in a appropriate anhydrous solvent such as tetrahydrofuran or diethyl ether using a suitable alkyl-lithium or metal e.g. butyllithium, lithium or magnesium turnings, followed by treatment with methyl iodide and the reaction may be performed at a reaction temperature within the range of –78° C. to room temperature, followed by cleavage of the benzyl groups by hydrogenation over a suitable catalyst containing palladium, rhodium, platinum or nickel, in a suitable solvent e.g. acetic acid or ethanol and at a reaction temperature between +20° C. and +120° C.

Method of Preparation of End Product.

Another object of the invention is a process for the preparation of the compound of the invention by acylation of a compound of formula XII,

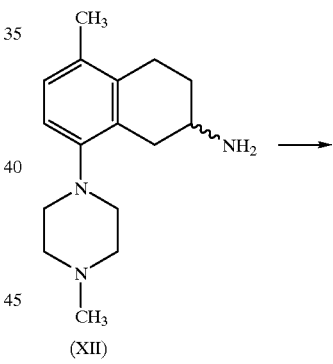
(XII)

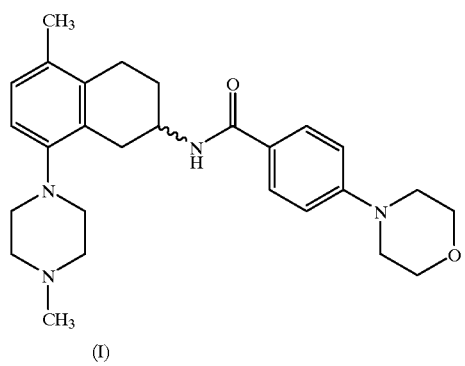
(I)

with activated 4-morpholinobenzoic acid and reacting the base with an organic or inorganic acid to form the salt with or without a solvate.

Thus, the acylation may be carried out by reacting the compound of formula XII with the acid chloride or acid bromide of 4-morpholinobenzoic acid in a suitable solvent such as methylene chloride or chloroform with a suitable base e.g. trialkylamine such as triethylamine at a temperature between −20° C. and reflux temperature or by activating the carboxylic acid function in 4-morpholinobenzoic acid with an activating reagent such as N,N'-carbonyldiimidazole, N,N'-dicyclohexylcarbodiimide or diphenylphosphinic chloride with or without a suitable base such as N-methylmorpholine in a suitable solvent such as N,N-dimethylformamide or tetrahydrofuran and the reaction may be conducted at a temperature between +20° C. and +150° C.

Furthermore, the pharmaceutically acceptable salt of the compound of the formula I may be obtained by reacting the base with the appropriate acid in a suitable solvent such as an alcohol e.g. methanol, ethanol or 2-propanol or another suitable solvent such as water, ethyl acetate, hexane, tetrahydrofuran, acetone, acetonitrile, chloroform or mixtures thereof. The process may be carried out at various temperatures between -30 and reflux. The salt formed in the above process may be formed as a solvate.

WORKING EXAMPLES

The following examples will describe, but not limit, the invention.

Example 1
(R)-2-N,N-Dibenzylamino-8-methoxy-1,2,3,4-tetrahydronaphthalene

To a solution of (R)-8-methoxy-2-amino-1,2,3,4-tetrahydronaphthalene hydrochloride (24 g, 0. 11 mol) in acetonitrile (600 mL) were added potassium carbonate (53 g, 0.39 mol), potassium iodide (catalytic amount) and benzyl bromide (34 mL, 0.28 mol). The reaction mixture was stirred at reflux for a period of 35 h.
After the precipitate was filtered off and the acetonitrile removed in vacuo, the residue was partitioned between diethyl ether and water. The organic phase was separated, dried ($Na_2SO_4$) and evaporated in vacuo to give a crude product which was purified on a silica gel column using hexane/ethyl acetate, (3:1) as the eluent. Yield: 36 g (91%) of the title compound as a white solid: mp 105–107° C.; $[a]^{21}_D$+124° (c 1.0, chloroform); EIMS (70 eV) m/z (relative intensity) 357 (100, M$^+$).

Example 2
(R)-7-N,N-Dibenzylamino-5,6,7,8-tetrahydro-1-naphthol (R)-2-N,N-Dibenzylamino-8-methoxy-1,2,3,4-tetrahydronaphthalene (43 g, 0.12 mol) was dissolved in diethyl ether (800 mL) and an excess of an ethereal HCl solution was added dropwise. The precipitate was filtered and dried in vacuo to give a white solid. This crude product (42 g, 0.11 mol) was dissolved in anhydrous methylene chloride (1 L) and cooled to −60° C. To the solution was boron tribromide (16 mL, 0.15 mol), dissolved in anhydrous methylene chloride (100 mL), added dropwise. The reaction temperature was allowed to reach −5° C. and was kept there overnight. To the ice-cooled solution was a 2 M aqueous ammonium hydroxide solution added dropwise and the mixture was extracted, twice, with methylene chloride. The combined organic phases were dried ($Na_2SO_4$), filtered and the solvent removed in vacuo to give a crude residue. Chromatography on silica (eluent: methylene chloride) gave 34 g (93% yield) of the title compound as a viscous clear oil: $[a]^{21}_D$+118° (c 1.5, chloroform); EIMS (70 eV) m/z (relative intensity) 343 (53, M$^+$).

Example 3
(R)-2-(7-N,N-Dibenzylamino-5,6,7,8-tetrahydro-1-naphthyloxy)-2-methylpropanamide (R)-2-N,N-Dibenzylamino-5,6,7,8-tetrahydro-1-naphthol (10 g, 29 mmol) was stirred in anhydrous dioxane (150 mL) with sodium hydride (80% in oil, 0.96 g, 32 mmol) for 1 h. 2-Bromo-2-methylpropanamide (4.8 g, 29 mmol; described in: Coutts, I. G. C.; Southcott, M. R. *J. Chem. Soc. Perkin Trans.* 1 1990, 767–770) was added and the reaction mixture was heated at 100° C. for 2.5 h. After cooling, the precipitated sodium bromide was filtered off, the filtrate evaporated in vacuo and the residue was partitioned between water and methylene chloride. The organic phase was separated, dried ($Na_2SO_4$), filtered and evaporated to give a crude product which was purified on a silica gel column using methylene chloride as the eluent. Yield: 9.6 g (76%) of the title compound as white crystals: mp 125–126° C.; $[a]^{21}_D$+98° (c 1.1, chloroform); EIMS (70 eV) m/z (relative intensity) 428 (13, M$^+$).

Example 4
(R)-N-(7-N,N-Dibenzylamino-5,6,7,8-tetrahydro-1-naphthyl)-2-hydroxy-2-methylpropanamide To a solution of (R)-2-(7-N,N-dibenzylamino-5,6,7,8-tetrahydro-1-naphthyloxy)-2-methylpropanamide (9.1 g, 21 mmol) in anhydrous 1,3-dimethyl-3,4,5,6-tetrahydro-2(1H)-pyrimidone (10 mL) and dry N,N-dimethylformamide (100 mL) was added sodium hydride (80% in oil, 1.4 g, 47 mmol) and the reaction was heated at 130° C. for 8 h. The solution was poured into a mixture of ice and water and extracted three times with ethyl acetate. The combined organic phases were dried ($Na_2SO_4$), filtered and evaporated in vacuo. Chromatography on silica (eluent: chloroform/ethanol saturated with $NH_3$; 100:0.5) gave 7.6 g (84% yield) as white crystals: mp 134–135° C.; $[a]^{21}_D$+130° (c 1.1, chloroform); EIMS (70 eV) m/z (relative intesity) 428 (1, M$^+$).

Example 5
(R)-2-N,N-Dibenzylamino-8-amino-1,2,3,4-tetrahydronaphthalene (R)-N-(7-N,N-Dibenzylamino-5,6,7,8-tetrahydro-1-naphthyl)-2-hydroxy-2-methylpropionamide (7.4 g, 17 mmol) was dissolved in a mixture of ethanol (200 mL) and a 20% HCl aqueous solution (300 mL) and heated to reflux for 8 h. The ethanol was evaporated in vacuo and the remaining solution was washed twice with diethyl ether and cooled on ice-bath. After alkalization with a 45% aqueous solution of sodium hydroxide the mixture was extracted with methylene chloride. The combined organic phases were dried ($Na_2SO_4$), filtered and evaporated in vacuo. Purification on a silica gel column using chloroform as the eluent gave 3.8 g (76% yield) of the title compound as a light-brown oil: $[a]^{21D}$+1240 (c 0.9, chloroform); EIMS (70 eV) m/z (relative intensity) 342 (92, M$^+$).

Example 6
(R)-1-(7-N,N-Dibenzylamino-5,6,7,8-tetrahydro-1-naphthyl)-4-N-methylpiperazine-2,6-dione 1,1'-Carbonyldiimidazole (6.0 g, 37 mmol) was added to a stirred suspension of methyliminodiacetic acid (2.7 g, 18 mmol) in anhydrous tetrahydrofuran (250 mL). The reaction mixture was heated at reflux for 1.5 h. (R)-2-N,N-Dibenzylamino-8-amino-1,2,3,4-tetrahydronaphthalene (5.7 g, 17 mmol) was then added and stirring at reflux was continued for 17 h. An additional amount of 1,1'-carbonyldiimidazole (2.9 g, 18 mmol) was added and heating at reflux was continued for another 17 h. The solvent was evaporated in vacuo and the crude product was purified on a silica gel column using chloroform/ethanol saturated with $NH_3$ (100:0.5) as the eluent. Yield: 6.6 g (87%) of the title compound as an oil: $[a]^{21D}+90°$ (c 0.52, chloroform); EIMS (70 eV) m/z (relative intensity) 453 (8, M$^+$).

Example 7
(R)-2-N,N-Dibenzylamino-8-(4-methylpiperazin-1-yl)-1,2,3,4-tetrahydronaphthalene (R)-1-(7-N,N-Dibenzylamino-5,6,7,8-tetrahydro-1-naphthyl)-4-methylpiperazine-2,6-dione (1.4 g, 3.1 mmol) was added to a suspension of lithium aluminium hydride (0.57 g, 15 mmol) in anhydrous diethyl ether (70 mL). The reaction mixture was heated at reflux for 7 h. The reaction was quenched by the addition of water (0.60 mL), 15% aqueous sodium hydroxide (0.60 mL) and again water (1.8 mL). The mixture was filtered, dried ($Na_2SO_4$) and evaporated in vacuo. Purification on a silica gel column using chloroform/ethanol saturated with $NH_3$ (100:2) as the eluent gave 1.0 g (79% yield) of the title compound as a viscous oil: $[a]^{21}_D+53°$ (c 0.5, chloroform); EIMS (70 eV) m/z (relative intensity) 425 (2, M$^+$).

Example 8
(R)-5-Bromo-2-N,N-dibenzylamino-8-(4-methylpiperazin-1-yl)-1,2,3,4-tetrahydronaphthalene.

To a solution of (R)-2-N,N-dibenzylamino-8-(4-methylpiperazin-1-yl)-1,2,3,4-tetrahydronaphthalene (2.8 g, 6.5 mmol) and sodium acetate (6.8 g, 83 mmol) in acetic acid (100 mL) was bromine (370 mL, 7.2 mmol) added in one portion and the reaction was stirred for 5 min. The solvent was evaporated in vacuo and the remaining solid was partitioned between water and methylene chloride and cooled on ice-bath. The water phase was alkalized with 2 M aqueous solution of sodium hydroxide and the phases were separated. The organic phase was dried ($Na_2SO_4$), filtered and evaporated in vacuo to give a crude product which was purified on a silica gel column using chloforn/ethanol saturated with $NH_3$ (100:2) as the eluent. Yield: 2 g (61%) of a viscous brown oil: EIMS (70 eV) m/z (relative intensity) 503 and 505 (0.6, M$^+$)

Example 9
(R)-2-N,N-Dibenzylamino-5-methyl-8-(4-methylpiperazin-1-yl)-1,2,3,4-tetra-hydronaphthalene (R)-2-N,N-Dibenzylamino-5-bromo-8-(4-methylpiperazin-1-yl)-1,2,3,4-tetra-hydronaphthalene (16 g, 0.31 mol) was dissolved in freshly distilled tetrahydrofuran (300 mL) and cooled to −78° C. under argon. To the solution was added n-butyl lithium (19 mL, 1.6 M in hexane, 0.31 mol,) dropwise during 45 min at a maximum temperature of −76° C. The dark green solution was stirred for an additional 20 min. A solution of methyl iodide (1.9 mL, 0.31 mol) in freshly distilled tetrahydrofuran (10 mL) was added dropwise during 25 min at a maximum temperature of −74° C. making the green color disappear. The reaction mixture was stirred at −78° C. for 50 min and at 0° C. for 50 min. The reaction was quenched with i-propylalcohol (3 mL) and the solvent was evaporated in vacuo. The residue was partitioned between ethyl acetate (300 mL) and $H_2O$ (30 mL) and the phases were separated and the organic layer was washed with brine (30 mL). After drying ($Na_2SO_4$), and evaporation of the solvent in vacuo, 15 g of a crude product was obtained. Purification by column chromatography on silica using ethyl acetate/triethylaamine (100:1) as the eluent afforded 11 g (82% yield) of the title compound as a brown oil: EIMS (70 eV) m/z (relative intensity) 439 (5, M$^+$); $[a]_D^{22}+86°$ (c 0.05, CHCl$_3$).

Example 10
(R)-2-Amino-5-methyl-8-(4-methylpiperazin-1-yl)-1,2,3,4-tetrahydro-naphthalene (R)-2-N,N-Dibenzylamino-5-methyl-8-(4-methylpiperazin-1-yl)-1,2,3,4-tetra-hydronaphthalene (28 g, 64 mmol) was dissolved in acetic acid (280 mL) and charged into a Büchi glass autoclave (1 L). 10% Palladium on charcoal (2.8 g, containing 50% $H_2O$) was added. The reaction mixture was stirred at 70° C. and at 5 bar hydrogen pressure for 3.5 h. The catalyst was filtered off and the solvent was evaporated in vacuo. The residue was partitioned between ethyl acetate (400 mL) and water (100 mL) and cooled on an ice-bath. The pH was adjusted to 12 by addition of aqueous NaOH (45%) and the phases were separated. The aqueous phase was re-extracted with ethyl acetate (2×100 mL) and the combined organic layer was washed with brine (50 mL) and dried ($Na_2SO_4$). Evaporation of the solvent in vacuo gave 18 g (99% yield) of the title compound as a brown oil. EIMS (70 eV) m/z (relative intensity) 259 (34, M$^+$); $[\alpha]_D^{22}-1.1°$ (c 0.09, CHCl$_3$).

Example 11
(R)-N-[5-Methyl-8-(4-methylpiperazin-1-yl)-1,2,3,4-tetrahydro-2-naphthyll-4-morpholinobenzamide 4-Morpholinobenzoic acid (23.3 g, 113 mmol; described in: Degutis, J.;Rasteikiene, L.; Degutiene, A. *Zh. Org. Khim.* 1978, 14(10), 2060–2064) and 1,1'-carbonyldiimidazole (19.2 g, 118 mmol) dissolved in anhydrous N,N-dimethylformarnide (250 mL), were stirred at 75° C. for 2 h and cooled to room temperature. To the solution was added (R)-2-amino-5-methyl-8-(4-methylpiperazin-1-yl)-1,2,3,4-tetrahydronaphthalene (27.8 g, 107 mmol) dissolved in anhydrous N,N-dimethylformamide (250 mL). The reaction mixture was stirred for 58 h giving a white slurry. The precipitate was filtered off and dried in vacuo giving 13.3 g of a crude product. The mother liquid was concentrated to dryness in vacuo giving 65 g of a crude material which was partitioned between $CH_2Cl_2$ (500 mL) and $H_2O$(70 mL). The organic layer was washed with $H_2O$ (70 mL) and brine (2×70 mL) and dried ($Na_2SO_4$). The solvent was evaporated in vacuo giving 40 g. The two portions were combined and recrystallized, three times, from anhydrous methanol to give 33.6 g (70% yield) of the title compound as white needles: mp 236–237° C.; EIMS (70 eV) m/z (relative intensity) 448 (3, M$^+$); $[\alpha]_D^{22}-60°$ (c 0.15, CHCl$_3$)
Salts of (R)-N-[5-Methyl-8-(4-methylpiperazin-1-yl)-1,2,3,4-tetrahydro-2-naphthyl]-4-morpholinobenzamide.

All melting points were determined using Differential Scanning Calorimetry (DSC). The temperature scanning rate was 10° C. per minute starting from room temperature. The samples were investigated in aluminum-pans with loose lids under nitrogen.

Example 12
(R)-N-[5-Methyl-8-(4-methylpiperazin-1-yl)-1,2,3,4-tetrahydro-2-naphthyl]-4-morpholinobenzamide L-Lactate.

To a warm solution of (R)-N-[5-methyl-8-(4-methylpiperazin-1-yl)-1,2,3,4-tetrahydro-2-naphthyl]-4-morpholinobenzamide (1.0 g, 2.2 mmol) in methanol (40 mL) was added L-lactic acid (240 mg, 2.7 mmol) and the solution was allowed to cool to room temperature. The solvent was evaporated in vacuo and the white residue was dissolved in 2-propanol (20 mL) under heating. After addition of diethyl ether (10 mL), the solution was allowed to cool to room temperature. The formed precipitate was filtered off and dried in vacuo to give 360 mg (30% yield) of the desired product as white crystals: mp 130–140° C. Anal. Calcd. for $C_{27}H_{36}N_4O_2 \times C_3H_6O_3$: C, 66.9; H, 7.9; N, 10.4. Found: C, 66.6; H, 7.9; N, 10.3.

Example 13

(R)-N-[5-Methyl-8-(4-methylpiperazin-1-yl)-1,2,3,4-tetrahydro-2-naphthyl]-4-morpholinobenzamide L-Ascorbate.

To a warm solution of (R)-N-[5-methyl-8-(4-methylpiperazin-1-yl)-1,2,3,4-tetrahydro-2-naphthyl]-4-morpholinobenzamide (1.0 g, 2.2 mmol) in methanol (30 mL) was added a solution of L-ascorbic acid (475 mg, 2.7 mmol) in methanol (20 mL) and the solution was allowed to cool to room temperature. About 25 mL of the solvent was evaporated in vacuo and the remaining solution (25 mL) was allowed to stand at room temperature for 2.5 h. The crystals were filtered and dried in vacuo to give 1.3 gram (92% yield) of the title compound as light grey crystals. mp 235–245° C. Anal. Calcd. for $C_{27}H_{36}N_4O_2 \times C_6H_8O_6 \times H_2O$: C, 61.7; H, 7.2; N, 8.7. Found: C, 61.9; H, 7.0; N, 8.9.

Example 14

(R)-N-[5-Methyl-8-(4-methylpiperazin-1-yl)-1,2,3,4-tetrahydro-2-naphthyl]-4-morpholinobenzamide Salicylate.

To a boiling solution of (R)-N-[5-methyl-8-(4-methylpiperazin-1-yl)-1,2,3,4-tetrahydro-2-naphthyl]-4-morpholinobenzamide (1.0 g, 2.2 mmol) in ethanol (50 mL) was added a solution of salicylic acid (400 mg, 2.9 mmol) in ethanol (10 mL). The solvent was concentrated in vacuo and the remaining solution (20 mL) was allowed to cool to room temperature. The solution was put in the freezer over the weekend. The crystals were filtered and dried in vacuo to give 1.2 gram (86% yield) of the title compound as white crystals: mp 235–240° C. Anal. Calcd. for $C_{27}H_{36}N_4O_2 \times C_7H_6O_3$: C, 69.6; H, 7.2; N, 9.6. Found: C, 69.5; H, 7.2; N, 9.5.

Example 15

(R)-N-[5-Methyl-8-(4-methylpiperazin-1-yl)-1,2,3,4-tetrahydro-2-naphthyl]-4-morpholinobenzamide Glycolate.

To a hot solution of (R)-N-[5-methyl-8-(4-methylpiperazin-1-yl)-1,2,3,4-tetrahydro-2-naphthyl)-4-morpholinobenzamide (1.0 g, 2.2 mmol) in ethanol (50 mL) was added a hot solution of glycolic acid (200 mg, 2.6 mmol) in ethanol (10 mL). The solvent was concentrated in vacuo and to the remaining solution (20 mL) was boiling ethyl acetate added until the solution was cloudy. After boiling for a few minutes, the solution was cooled and put in the refrigerator over night. The crystals were filtered and dried in vacuo to give 1.0 gram (83% yield) of the title compound as white crystals. Anal. Calcd. for $C_{27}H_{36}N_4O_2 \times C_7H_6O_3 \times 2H_2O$: C, 62.1; H, 7.9; N, 10.0. Found: C, 62.7; H, 7.7; N, 9.6.

Example 16

(R)-N-15-Methyl-8-(4-methylpiperazin-1-yl)-1,2,3,4-tetrahydro-2-naphthyl]-4-morpholinobenzamide Dihydrobromide (R)-N-[5-Methyl-8-(4-methylpiperazin-1-yl)-1,2,3,4-tetrahydro-2-naphthyl]-4-morpholinobenzamide (2.0 g, 4.5 mmol) was dissolved in anhydrous tetrahydrofuran (55 mL) and an ethereal HBr solution was added until the solution was acidic. The white solid was filtered, washed with diethyl ether and dried to give the crude solid. The crude solid was recrystallized from absolute ethanol/ethyl acetate to give 0.78 g (29% yield) of white transparent crystals: mp 250–265° C. Anal. Calcd. for $C_{27}H_{38}Br_2N_4O_2$: C, 53.1; H, 6.3;

Br, 26.2; N, 9.2. Found: C, 53.0; H, 6.4; Br, 26.3; N, 9.0.

Example 17

(R)-N-15-Methyl-8-(4-methylpiperazin-1-yl)-1,2,3,4-tetrahydro-2-naphthyl]-4-morpholinobenzamide Dihydrochloride (R)-N-[5-Methyl-8-(4-methylpiperazin-1-yl)-1,2,3,4-tetrahydro-2-naphthyl]-4-morpholinobenzamide (2.0 g, 4.5 mmol) was dissolved in anhydrous tetrahydrofuran (55 mL) and an ethereal HCl solution was added until the solution was acidic. The white solid was filtered, washed with diethyl ether and dried to give a crude hygroscopic solid. The crude solid was recrystallized, twice, from ethanol/ethyl acetate to give 0.11 g (16% yield) of small hard white crystals. Anal. Calcd. for $C_{27}H_{38}Cl_2N_4O_2$: C, 62.2; H, 7.3; Cl, 13.6; N, 10.7. Found: C, 62.1; H, 7.4; Cl, 13.4; N, 10.8.

Example 18

(R)-N-[5-Methyl-8-(4-methylpiperazin-1-yl)-1,2,3,4-tetrahydro-2-naphthyl-1-4-morpholinobenzamide Monohydrobromide.

Imidazole (16.3 g, 239 mmol) was dissolved in isopropanol (170 mL) and hydrobromic acid (34% w/w in acetic acid, 49.5 mL, 218 mmol) was added dropwise. This solution was added to a slurry of (R)-N-[5-methyl-8-(4-methylpiperazin-1-yl)-1,2,3,4-tetrahydro-2-naphthyl]-4-morpholinobenzamide (89.2 g, 198 mmol) in isopropanol (710 mL) at 40° C. After the addition was complete the mixture was heated to reflux for 3 h. After cooling to 0° C. the crystals were collected by filtration and dried at 60° C. under vacuum to give 98.5 g (93.6% yield) of crude monohydrobromide.

The crude monohydrobromide above (96.6 g, 182 mmol) was recrystallized from 95% ethanol (5% water v/v, 598 mL) and ethyl acetate (2280 mL) at 60–70° C. and the slurry was slowly cooled to −10° C. before filtration. The crystals were collected by filtration and dried at 60° C. under vacuum to give 87.7 g (91% yield) of slightly pink crystals: mp 265° C. (decom.). $^1$H NMR (300 MHz, DMSO-d$_6$)δ8.24 (d, J=7.5 Hz, 1 H), 7.86 (d, J=8 Hz, 2 H), 6.92–7.08 (m, 1H), 7.01 (d, J=7.5 Hz, 1 H), 6.98 (d, J=8 Hz, 1 H), 6.86 (d, J=8 Hz, 1 H), 3.61–4.07 (m, 5 H), 2.42–3.61 (m, 16 H), 2.84 (s, 3 H), 2.00–2.20 (m, 1 H), 2.15 (s, 3 H), 1.63–1.88 (m, 1H).

Pharmacology

Electrical field stimulation of [$^3$H] -5-HT release from occipital cortex of guinea pigs [$^3$H] -5-HT is released by electrical field stimulation from slices of occipital cortex of guinea pigs which have been pre-incubated with [$^3$H] -5-HT. This release is similar to that caused by nerve stimulation, i.e. exocytotical release from serotonergic nerve terminals, depending on the presence of $Ca^{2+}$ in the incubation medium. The 5-HT release is regulated at the level of the nerve terminals by autoreceptors, in the guinea pigs (like in humans) belonging to the h5-HT$^{1B}$ receptor subtype. Thus, agonists of h5-HT$^{1B}$ receptors reduce the amount of [3H]-5-HT released by field stimulation whereas the release is increased by antagonists of this receptor type. Testing compounds with this method is accordingly a convenient screening technique for determining the potency and functional effect of new h5-HTIB receptor agonists and antagonists.

Methods and Materials

Buffer composition (mM) NaHCO$_3$ (25), NaH$_2$PO$_4$·H$_2$O (1.2), NaCl (117), KCl(6), MgSO$_4$×7H$_2$O(1.2), CaCl$_2$(1.3), EDTA Na$_2$(0.03). The buffer is gassed for at least 30 min before use. The pH of the buffer is about 7.2 at room temperature but it rises to about 7.4 at 37° C.

Preparation of Occipital Cortical Slices

Guinea pigs (200–250 g) were decapitated and the whole brain was removed. The occipital cortex was dissected and cut to slices 0.4×4 mm with McIlwain chopper machine. The white part of the tissue should be removed carefully with a tweezers before slicing. The slices were incubated in 5 ml buffer in the presence of 5 mM pargyline chloride. After incubation with 0.1 mM [$^3$H]-5-HT for another 30 min the slices were transferred to a test tube and washed three times with same volume buffer. The slices were transferred to the superfusion chambers with a plastic pipette and were washed for 40 min with the buffer in the presence of uptake inhibitor citalopram 2.5 μM with a flow 0.5 ml/min.

Electrical Stimulation of 5-HT Release

The superfused buffer was collected in 2 mL fractions. The slices were stimulated by electricity with a train of pulses of frequency 3 Hz, duration 2 ms and current 30 mA for 3 min at the 4th and 13th fractions. The tested drugs were added from the 8th fraction to the end of experiment.

Results

A first electrical (or K$^+$) stimulation results in a standard amount of [$^3$H]-5-HT released (S1). Between the first and a second stimulation the h5-HT$_{1B}$ antagonist is added to the media which results in a dose depending increase of the release(S$_2$) after the second stimulation. See FIG. 1.

The S$_2$/S$_1$ ratio which is the per cent of released [$^3$H]-5-HT at the second stimulation (S$_2$) divided by that of the first stimulation (S$_1$) was used to estimate drug effects on transmitter release.

Solubility Determination of (R)-N-15-Methyl-8-(4-Methylpiperazin-1-yl)-1,2,3,4-Tetrahydro-2-Naphthyl]-4-Morpholinobenzamide and it's corresponding Salts.

Method

Excess of (R)-N-[5-methyl-8-(4-methylpiperazin-1-yl)-1,2,3,4-tetrahydro-2-naphthyl]-4-morpholinobenzamide or it's corresponding salts was added to purified water. The solution was agitated overnight in a water bath, kept at 25° C. by using a thermostat (Julabo SW and U3, 60 strokes/min). The saturated solution was centrifuged and filtered through a 0.45 □m Gelman GHP Acrodisc® 13 filter, diluted and assayed by HPLC.

Results

Solubility in Water at 25° C. for the Base, (R)-N-[5-Methyl-8-(4-Methylpiperazin-1-yl)-1,2,3,4-Tetrahydro-2-Naphthyl]-4-Morpholinobenzamide.

0.034 mg/mL

Solubility in Water at 25° C. for different salts of (R)-N-[5-Methyl-8-(4-Methylpiperazin-1-yl)-1,2,3,4-Tetrahydro-2-Naphthyl]-4-Morpholinobenzamide.

| Salt (Example) | Solubility mg/mL |
| --- | --- |
| L-Lactate | 18.8 |
| L-Ascorbate | 4.2 |
| Salicylate | 0.29 |
| Glycolate | >23.6 |
| Dihydrobromide | 4.6 |

It is clear from the above comparison between the base compound and a number of representaive salts thereof that salts of the compound according to formula (I) to a greater extent are more soluble in water compared to the base and thus are more suitable for preparing pharmaceutical formulations.

What is clamed is:

1. A pharmaceutically acceptable salt of the compound of formula I or a solvate of said salt in which the compound of formula I is as the (R)-enantiomer, the (S)-enantiomer or the racemate

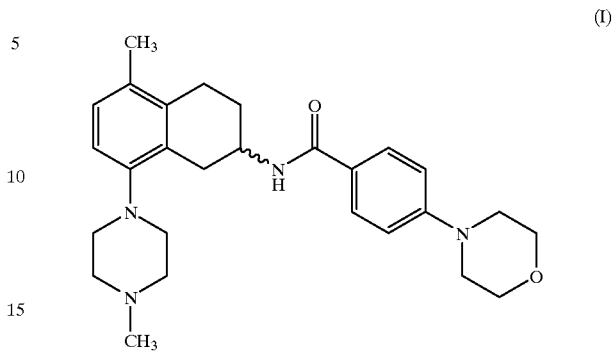

with the proviso that
(R)-N-[5-methyl-8-(4-methylpiperazin-1-yl)-1,2,3,4-tetrahydro-2-naphthyl]-4-morpholinobenzamide hydrogen (2S,3S)-tartrate,
(R)-N-[5-methyl-8-(4-methylpiperazin-1-yl)-1,2,3,4-tetrahydro-2-naphthyl]-4-morpholinobenzamide hydrogen (2R,3R)-tartrate,
(R)-N-[5-methyl-8-(4-methylpiperazin-1-yl)-1,2,3,4-tetrahydro-2-naphthyl]-4-morpholinobenzamide benzenesulfonate,
(R)-N-[5-methyl-8-(4-methylpiperazin-1-yl)-1,2,3,4-tetrahydro-2-naphthyl]-4-morpholinobenzamide hydrogen 1,2-ethanedisulfonate,
(R)-N-[5-methyl-8-(4-methylpiperazin-1-yl)-1,2,3,4-tetrahydro-2-naphthyl]-4-morpholinobenzamide hydrogen maleate,
(R)-N-[5-methyl-8-(4-methylpiperazin-1-yl)-1,2,3,4-tetrahydro-2-naphthyl]-4-morpholinobenzamide hydrogen sulfate,
(R)-N-[5-methyl-8-(4-methylpiperazin-1-yl)-1,2,3,4-tetrahydro-2-naphthyl]-4-morpholinobenzamide D-gluconate,
(R)-N-[5-methyl-8-(4-methylpiperazin-1-yl)-1,2,3,4-tetrahydro-2-naphthyl]-4-morpholinobenzamide hydrogen succinate,
(R)-N-[5-methyl-8-(4-methylpiperazin-1-yl)-1,2,3,4-tetrahydro-2-naphthyl]-4-morpholinobenzamide methanesulfonate,
(R)-N-[5-mnethyl-8-(4-methylpiperazin-1-yl)-1,2,3,4-tetrahydro-2-naphthyl]-4-morpholinobenzamide hydrogen (S)-maleate,
(R)-N-[$^5$-methyl-8-(4-methylpiperazin-1-yl)-1,2,3,4-tetrahydro-2-naphthyl]-4-morpholinobenzamide dihydrogen citrate and
(R)-N-[$^5$-methyl-8-(4-methylpiperazin-1-yl)-1,2,3,4-tetrahydro-2-naphthyl]-4-morpholinobenzamide hydrochloride are excluded.

2. A pharmaceutically acceptable salt according to claim 1 in which the compound of formula I is an (R)-enantiomer or a solvate of said salt.

3. A salt or solvate according to claim 1 which is (R)-N-[5-methyl-8-(4-methylpiperazin-1-yl)-1,2,3,4-tetrahydro-2-naphthyl]-4-morpholinobenzamide L-lactate or a solvate thereof.

4. A salt or solvate according to claim 1 which is (R)-N-[5-methyl-8-(4-methylpiperazin-1-yl)-1,2,3,4-tetrahydro-2-naphthyl]-4-morpholinobenzarnide L-ascorbate or a solvate thereof.

5. A salt or solvate according to claim 1 which is (R)-N-[5-methyl-8-(4-methylpiperazin-1yl)-1,2,3,4-tetrahydro-2-naphthyl]-4-morpholinobenzamide salicylate or a solvate thereof.

6. A salt or solvate according to claim 1 which is (R)-N-[5-methyl-8-(4-methylpiperazin-1-yl)-1,2,3,4-tetrahydro-2-naphthyl]-4-morpholinobenzamide glycolate or a solvate thereof.

7. A salt or solvate according to claim 1 which is R)-N-[5-Methyl-8-(4-methylpiperazin-1-yl)-1,2,3,4-tetrahydro-2-naphthyl]-4-morpholinobenzamide dihydrobromide or a solvate thereof.

8. A salt or solvate according to claim 1 which is R)-N-[5-methyl-8-(4-methylpiperazin-1-yl)-1,2,3,4-tetrahydro-2-naphthyl]-4-morpholinobenzamide monohydrobromide or a solvate thereof.

9. A salt or solvate according to claim 1 which is R)-N-[5-Methyl-8-(4-methylpiperazin-1-yl)-1,2,3,4-tetrahydro-2-naphthyl]-4-morpholinobenzamide dihydrochloride or a solvate thereof.

10. A pharmaceutical formulation comprising as active ingredient a therapeutically effective amount of the salt or solvate according to any one of claims 1–9 or a combination of such salts and/or solvates, optionally in association with diluents, excipients or inert carriers.

11. A method for the treatment of 5-hydroxytryptamine mediated disorders, comprising administering to a patient in need of such treatment the pharmaceutical formulation according to claim 10.

12. A method for the treatment of mood disorders, anxiety disorders, personality disorders, obesity, anorexia, bulimia, premenstrual syndrome, sexual disturbances, alcoholism, tobacco abuse, autism, attention deficit, hyperactivity disorder, migraine, memory disorders, pathological aggression, schizophrenia, endocrine disorders, stroke, dyskinesia, Parkinson's disease, thermoregulatory disorders, pain, hypertension, urinary incontinence or vasospasm; or for inhibiting growth of tumors, comprising administering to a patient in need of such treatment the pharmaceutical formulation according to claim 10.

13. A method according to claim 12 for the treatment of major depressive disorder.

14. A method for the treatment of disorders in the central nervous system, comprising administering to a patient in need of such treatment a therapeutically effective amount of a salt or solvate as defined in any one of claims 1–9.

15. A method for the treatment of urinary incontinence or vasospasm or for inhibiting growth of tumors, comprising administering to a patient in need of such treatment a therapeutically effective amount of a salt or solvate as defined in any one of claims 1–9.

16. A method according to claim 14 for the treatment of mood disorders, anxiety disorders, personality disorders, obesity, anorexia, bulimia, premenstrual syndrome, sexual disturbances, alcoholism, tobacco abuse, autism, attention deficit, hyperactivity disorder, migraine, memory disorders, pathological aggression, schizophrenia, endocrine disorders, stroke, dyskinesia, Parkinson's disease, thermoregulatory disorders, pain or hypertension.

17. A method according to claim 16 for the treatment of major depressive disorder.

18. A method for the treatment of 5-hydroxytryptamine mediated disorders, comprising administering to a patient in need of such treatment a therapeutically effective amount of a salt or solvate as defined in any one of claims 1–9.

19. A method according to claim 18 wherein the disorder is effectively treated with a h5-$HT_{1B}$ antagonist.

20. A process for the preparation of the salt of the compound of formula I or the solvate of said salt according to claim 1, comprising acylation of a compound of formula XII,

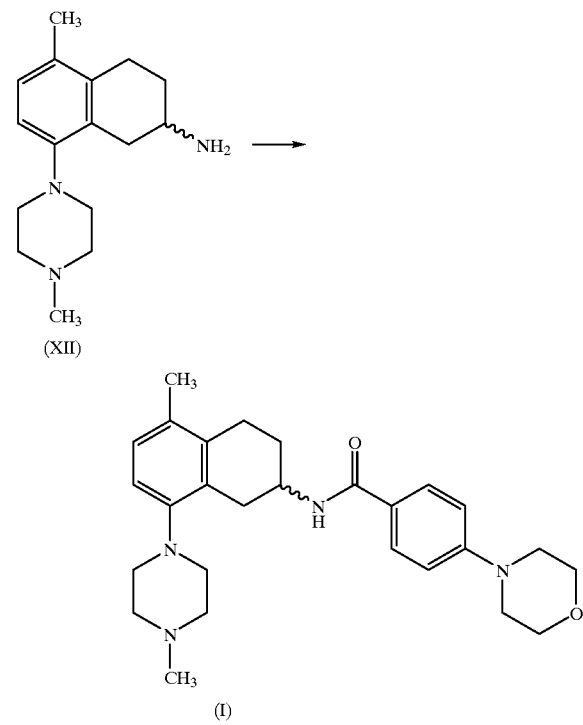

with activated 4-morpholinobenzoic acid and reaction of the base with an organic or inorganic acid to form the salt with or without a solvate.

* * * * *

UNITED STATES PATENT AND TRADEMARK OFFICE
CERTIFICATE OF CORRECTION

PATENT NO. : 6,291,458 B1
DATED : September 18, 2001
INVENTOR(S) : Berg et al.

It is certified that error appears in the above-identified patent and that said Letters Patent is hereby corrected as shown below:

<u>Title page,</u>
Item [30], Foreign Application Priority Data, delete "July 2, 1997" and substitute therefor -- July 25, 1997 --.

<u>Column 1,</u>
Line 37, delete "ring, said class or compounds" and substitute therefor -- ring. Said class of compounds --.
Line 41, delete "group, said" and substitute therefor -- group. Said --.
Line 46, delete "ring, said" and substitute therefor -- ring. Said --.

<u>Column 13,</u>
Lines 51, 53 and 56, (three instances), delete "0.31" and substitute therefor -- 0.031 --.

<u>Column 14,</u>
Line 28, delete "napthyll" and substitute therefor -- naphthyl] --.

<u>Column 16,</u>
Line 51, delete "serotonergic" and substitute therefor -- serotoninergic --.

<u>Column 17,</u>
Line 3, delete "brain was" and substitute -- brains were --.
Line 3, delete "cortex was" and substitute therefor -- cortices were --.
Line 25, insert -- , -- after "ratio".
Line 27, insert -- , -- after "($S_1$)".
Line 31, delete "it's" and substitute therefore -- its --.
Line 33, delete "Excess" and substitute therefor -- An excess --.
Line 35, delete "it's" and substitute therefor -- its --.

UNITED STATES PATENT AND TRADEMARK OFFICE
CERTIFICATE OF CORRECTION

PATENT NO.   : 6,291,458 B1
DATED        : September 18, 2001
INVENTOR(S)  : Berg et al.

It is certified that error appears in the above-identified patent and that said Letters Patent is hereby corrected as shown below:

Column 18,
Line 45, delete "mnethyl" and substitute therefor -- methyl --.
Lines 48 and 51, delete "$^5$-methyl" and substitute therefor -- 5-methyl --.
Line 54, insert "," after -- enantiomer --.
Line 61, delete "morpholinobenzarnide" and substitute therefore
-- morpholinobenzamide --.
In each of the following locations, delete "or solvate":
col. 18, line 57;
col. 18, line 61;
col. 18, line 65;
col. 19, line 1;
col. 19, line 5;
col. 19, line 9; and
col. 19, line 13.

Signed and Sealed this

Twenty-fourth Day of December, 2002

JAMES E. ROGAN
*Director of the United States Patent and Trademark Office*